United States Patent [19]

Flomenblit et al.

[11] Patent Number: 5,667,522
[45] Date of Patent: Sep. 16, 1997

[54] UROLOGICAL STENT AND DEPLOYMENT DEVICE THEREFOR

[75] Inventors: Josef Flomenblit; Nathaly Budigina, both of Holon, Israel

[73] Assignee: Medinol Ltd., Tel Aviv, Israel

[21] Appl. No.: 397,674

[22] Filed: Mar. 2, 1995

[30] Foreign Application Priority Data

Mar. 3, 1994 [IL] Israel ......... 108832

[51] Int. Cl.$^6$ ......... A61M 29/00
[52] U.S. Cl. ......... 606/198; 606/191
[58] Field of Search ......... 606/198, 191, 606/194, 195, 108, 192; 604/96

[56] References Cited

U.S. PATENT DOCUMENTS

| | | |
|---|---|---|
| 4,503,569 | 3/1985 | Dotter . |
| 4,762,128 | 8/1988 | Rosenbluth ......... 606/192 |
| 4,795,458 | 1/1989 | Regan et al. . |
| 4,969,890 | 11/1990 | Sugita et al. ......... 606/194 |
| 5,037,427 | 8/1991 | Harada et al. . |
| 5,147,370 | 9/1992 | McNamara et al. . |

FOREIGN PATENT DOCUMENTS

| | | |
|---|---|---|
| 2512678 | 9/1982 | France . |
| 2617721 | 7/1988 | France . |
| WO93/13824 | 7/1993 | WIPO . |

*Primary Examiner*—Michael Buiz
*Assistant Examiner*—Kevin Truong
*Attorney, Agent, or Firm*—Nath & Associates; Gary M. Nath

[57] ABSTRACT

A stent adapted for placing in the urethra so as to retain the urethra's diameter above a critical level is provided. The stent comprises:

a spiral band made of a two-way shape memory alloy having two memory states consisting of a first state in which said alloy is soft and substantially deformable and a second state in which the alloy has super elastic properties and is substantially non-deformable, the alloy changes from the fast state to the second state at a first transition temperature being above physiological body temperature and changes from the second to the first state at a second transition temperature being below physiological body temperature; in the second state consecutive windings of the band are adjacent one another so that they form together essentially a continuous cylindrical tube of a diameter above said critical level; in the first state the band forms a coiled structure having a maximal external diameter such so as to allow deployment of stent within the urethra.

6 Claims, 4 Drawing Sheets

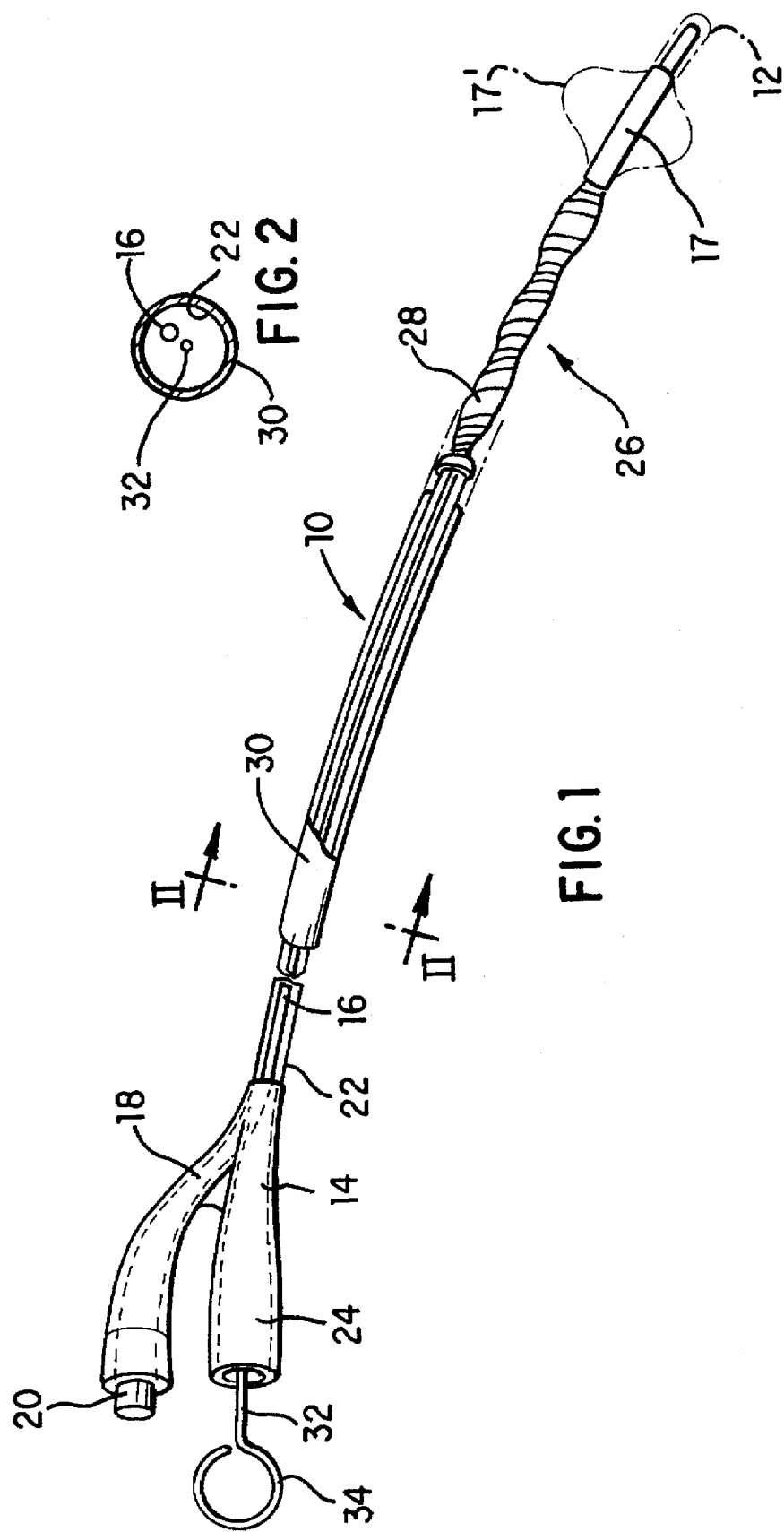

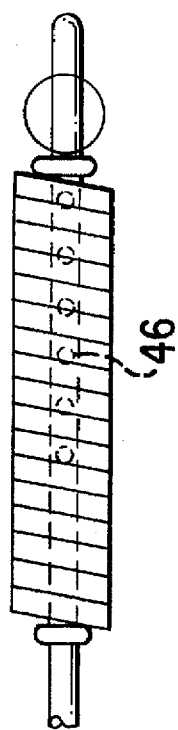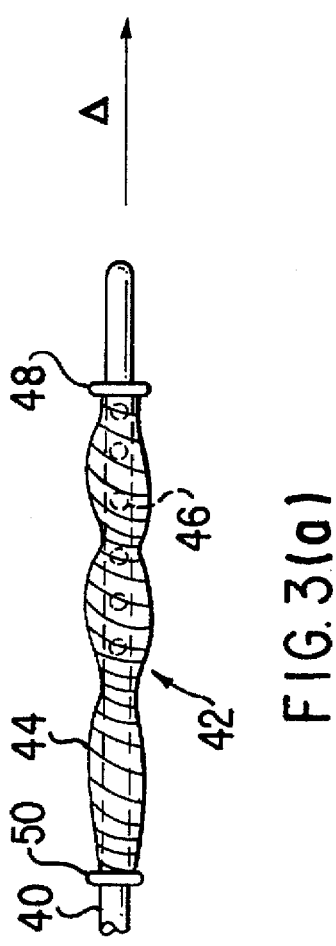
FIG.3(a)  FIG.3(b)
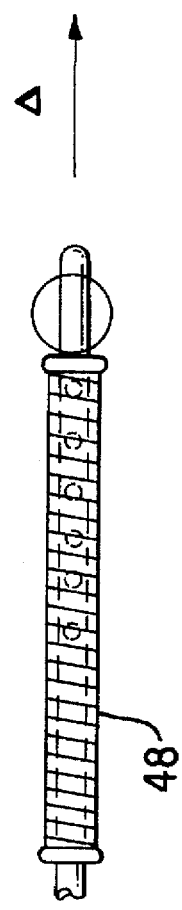
FIG.4(a)  FIG.4(b)

UROLOGICAL STENT AND DEPLOYMENT DEVICE THEREFOR

FIELD OF THE INVENTION

The present invention concerns a stent intended for placing inside the urethra.

The present invention also provides a device for deployment of the stent.

BACKGROUND OF THE INVENTION

In some clinical situations it is necessary to intervene to ensure that the urethra remains open. Such is the case, for example, in various pathologies associated with swelling of the prostate in males. One means for achieving this is by deploying a stent at the appropriate place inside the urethra.

Stents are typically made of a helical wire or band which once deployed inside a tubular organ expands to the desired diameter thereby supporting the walls of the organ. U.S. Pat. No. 5,037,427 discloses a stent made of a two-way shape memory alloy and means for its deployment in and recovery from a tubular organ. The stent in accordance with this patent has a transition temperature which is below the body temperature in which it changes in diameter from a narrow diameter to a wide diameter in which it attaches to the walls of the tubular organ. The stent is inserted into the tubular organ under a constant flow of cold fluid and once the correct position of the stent is reached, the flow of the cold fluid is stopped and the stent then expands under the influence of the body temperature. For removal, the stent is cooled again and withdrawn under a continuous application of cold fluid. It will no doubt be appreciated that a continuous application of a cold fluid may not always be practicable and this is a continuous drawback for various applications.

PCT Application, WO 93/13824, discloses a segmentally expandable stent comprising a helically coiled structure shaped wire of an nickel-titanium alloy (Nitinol™). In its primary shape its diameter in at least a portion is wide so as to support the walls of the urethra and in its other state the diameter is reduced to an extent allowing insertion of the stent into the urethra. The stent is designed in a manner that it does not change in length upon expansion. However, the big disadvantage of such a stent is in that the wires press on the surrounding tissue at relatively large local pressure which can damage this delicate tissue. Furthermore, after some times of being within the urethra, there is a growth of tissue in the gaps between the wires, which hinders easy removal of the stent.

Placing a stent in the appropriate place in the urethra poses a special problem to the practitioner of proper localization. For example, in male subjects suffering from a prostate enlargement, it is necessary to place the stent at the right zone of the urethra within the prostate as improper placement will not yield the desired result of ensuing urine drainage.

It is an object of the present invention to provide a novel urological stent. It is particularly an object of the invention to provide such a stent which can be easily deployed in the urethra and easily removed therefore.

It is another object of the invention to provide a device adapted for deployment of the stent within the urethra in a manner which will ensure proper positioning of the stent.

GENERAL DESCRIPTION OF THE INVENTION

The present invention provides, by its first aspect, a stent adapted for placing in the urethra so as to retain the urethra's diameter above a critical level, comprising:

a spiral band made of a two-way shape memory alloy having two memory states consisting of a first state in which said alloy is soft and substantially deformable and a second state in which said alloy has super elastic properties and is substantially non-deformable, the alloy changes from the first state to the second state at a first transition temperature being above physiological body temperature and changes from the second to the first state at a second transition temperature being below physiological body temperature; in said second state consecutive windings of the band are adjacent one another so that they form together essentially a continuous cylindrical tube of a diameter above said critical level; in said first state said band forms a coiled structure having a maximal external diameter such so as to allow deployment of stent within the urethra.

During expansion, a stent consisting of one layer of windings, shrinks in length. This causes a longitudinal displacement which may damage the surrounding tissue. Consequently, in accordance with a preferred embodiment of the invention, the windings of the stent in its first state are at least partially overlapping whereby the total length of the stent does not change during transition from the first to the second state.

By a second of its aspects, the present invention provides a device for deployment of a stent in a predetermined part of the urethra, comprising:

a catheter having a front end adapted for insertion into the urethra and a rear end, and comprising at least one pressure tube and at least one liquid ducting tube; said pressure tube being connected to an expandable balloon and which is proximal to the from end of the catheter and which is adapted for expansion within the bladder; said pressure tube being connectable at its rear end to a source of pressurized fluid; said liquid ducting tube having openings at a portion there, of rearward to and at a distance from said balloon being connectable at its rear end to a liquid source; said portion being adapted for holding a stent coiled thereon; the part of the urethra where said stent is being deployed being determined by said distance.

Typically, said first tube is held within said second tube, there being a space between the external walls of said first tube and the internal walls of said second tube to allow passage of liquid therethrough from the rear end of said second tube to the openings.

The catheter may comprise a retractable sleeve adapted to cover the stent when coiled on said portion prior to deployment thereof.

The catheter of the invention may be used for the deployment of both stents of the invention as defined above, as well as a prior art stent, e.g. such wherein the transition temperature in which it switches from the first to the second state is below physiological body temperature, i.e. such which spontaneously assumes a second, superelastic state at body temperature.

For deployment of a stent, the front end of the catheter is inserted through the urethra until it comes to rest within the bladder. Once in this position, which position can be asserted by a number of means as readily known per se, pressurized fluid is applied to the pressure tube and consequently the balloon expands within the bladder. Following expansion, the catheter is slightly retracted until the balloon comes to rest against the bladder neck. Where the stem is a stem of the invention, after the balloon comes to rest as aforesaid, warm fluid is injected through the liquid ducting tube, and this warm liquid exiting through the openings at said portion brings to expansion of the stent (as a result of its changing from the first to the second state) and the stent is thus deployed within the urethra. The portion within the method where the stent is deployed depends on the distance between the balloon and the portion of the catheter on which the stent is held. Where the stent is a prior art stent of the kind mentioned above, during the entire insertion process, cooled liquid is injected through the liquid ducting tube so as to avoid expansion of the stent, and after proper positioning of the catheter, the injection of this liquid stops and the stem thus expands as a result of being heated to body temperature.

The invention will now be illustrated in the following description of the specific embodiments with occasional reference to the annexed drawings.

BRIEF DESCRIPTION OF THE DRAWINGS

FIG. 1 shows a stent deployment device according to an embodiment of the invention holding a stent prior to its deployment;

FIG. 2 is a cross-section through lines II—II in FIG. 1;

FIG. 3 shows the manner of expansion of a stent of the kind shown in FIG. 1;

FIG. 4 shows the manner of expansion of a stent according to another embodiment.

DESCRIPTION OF SPECIFIC EMBODIMENTS

Figure 5A:
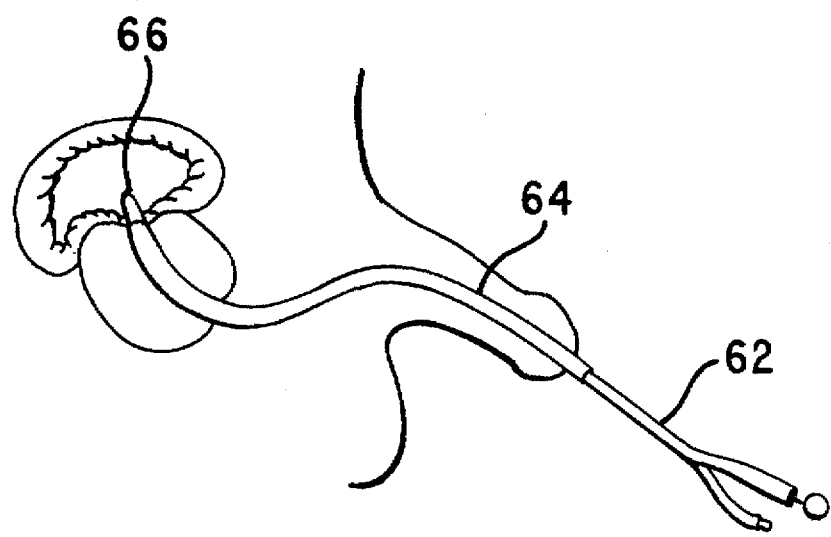
FIG. 5 shows sequences of deployment of a stent of the invention within a prostate.
Figure 5B:
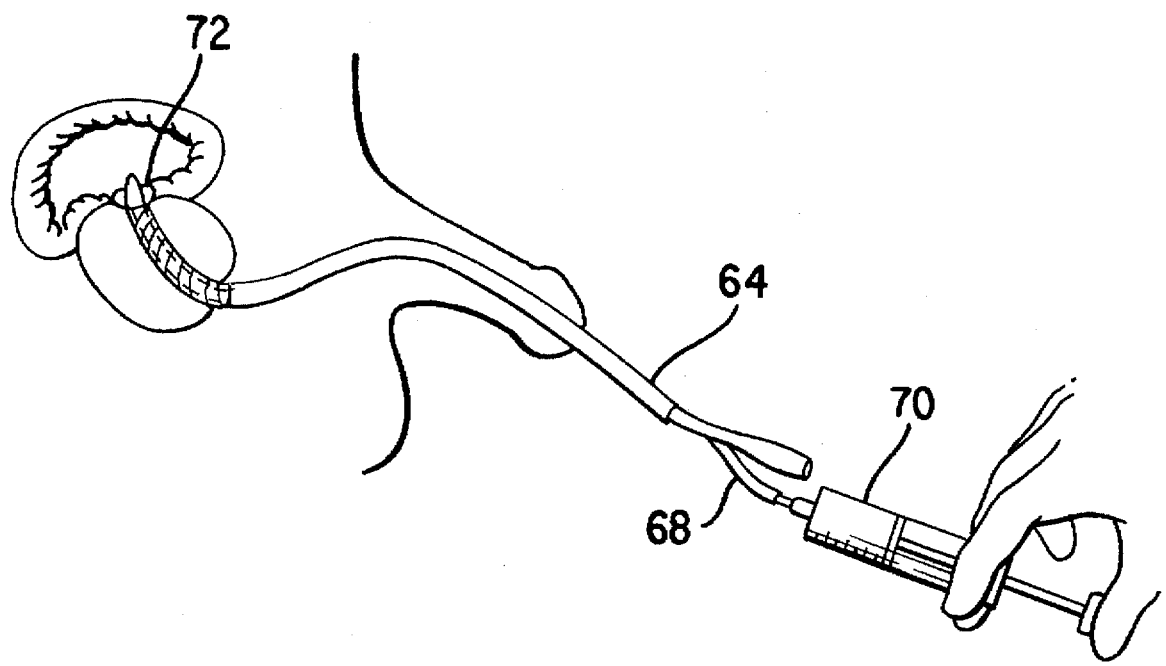

The stem of the present invention can be made of a variety of two-way shape memory alloys (SMA) such as Ni-Ti binary alloy, known as "Nitinol", Ni-Ti-X (X being V, Co, Cu, Fe, Cr) ternary alloy, Cu-Al-Ni ternary alloy, or Cu-Zn-Al ternary alloy. A two-way SMA has two basic states: the martensitic state, which is a state assumed by the alloy at low temperatures, and an austenitic state, assumed by the alloy at high temperatures (in the austenitic state the SMA has also so-called "super elasticity", meaning that the elasticity is practically independent on deformation over a range of deformations). The transition between the martensitic state to the austenitic state, i.e., the austenitic transformation, begins at a certain temperature, referred to in the art as "$A_s$," and ends at a temperature referred to in the art as "$A_f$" ($A_f > A_s$). The reverse transformation between the austenitic to the martensitic state begins at a temperature $M_s$ and ends at temperature $M_f$ ($M_s > M_f$).

In the description above and further below, reference is made to "transition temperature", but this does not mean to denote that the transition occurs at a singe well defined temperature. This term is used for the ease of description, it being understood that transition temperature is in fact a temperature range $A_s$ to $A_f$ for the first transition and a temperature range $M_s$ to $M_f$ for the second transition.

The stent in accordance with the invention is preferably made of an SMA with a chemical composition, represented by the following formula:

$$Ni_j Ti_m A_n$$

wherein

A represents Ni, Co, Fe, Cr or V l, m, and n representing the proportions of the metal ions within the alloy, the value of l, m and n totalling 1 and being about as follows:

l=0.5 m=0.5−n n=0.003 to 0.02.

The band of the stent has typically a width of about 1.0–6.0 mm and a thickness of about 0.1–0.5 mm.

A two-way shaped memory alloy of the kind used in accordance with the invention has two transition temperatures: a first transition temperature being above physiological body temperature in which it changes from its first state, in which the alloy is relatively ,soft and deformable, to its second state, in which the alloy is substantially harder and has super elastic properties; and a second transition temperature, being below body temperature, in which it changes from said second state to said first state. The first transition temperature is typically within the range of 37°–80° C., preferably within the range of 39°–55° C., while the second transition temperature is typically within the range of −10°–+35° C., preferably within the range of 20°–32° C. The alloy is typically made so that the transition occurs over a narrow temperature range, the difference between $A_f$ and $A_s$ being preferably about 1°–4° C. The advantage of having a narrow temperature range is that the transition between the two states is relatively rapid and danger of tissue overheating decreases. The super elastic properties of the stent in said second state are manifested in that the stent exert substantially constant pressure to the surrounding tissue.

In the first state, the device is coiled tightly onto the catheter and following injection of a warm fluid through the openings, the catheter expands and is thus deployed within a respective portion of the urethra. A stent of the invention intended for deployment within the prostrate has typically a maximal diameter prior to deployment of about 3–7 mm and after being heated expands to form a tube having a diameter of about 8–14 mm.

It is preferable at times that the stent, in its second state will have a portion of a larger diameter than the rest of the stent. For example, the stent can at times be made to have at least one loop with a diameter of about 1–5 mm larger than other parts of the stent. This is important at times for anchoring the stent to prevent unwanted displacement of the stent.

Reference is now being made to FIGS. 1 and 2 showing a stent deployment device of an embodiment of the invention. The stem generally designated 10 is a catheter having a front end 12 adapted for insertion into the urethra and a rear end 14. The catheter comprises a pressure tube 16 connected at its front end to an expandable balloon 16 and terminating at its rear end 18 at a connector 20 to which a syringe (not shown) may be fitted for the application of pressure. Upon the application of pressure, balloon 17 expands to the state 17' represented by a dotted line in the figure.

Pressure tube 16 is held within a tube 22 having a connector 24 at its rear end adapted for connecting to a liquid source, e.g. a large syringe and terminating at its front end at a plurality of openings (not shown in this figure) at the portion thereof generally designated 26. Portion 26 holds a stent 28 coiled thereon in its soft state.

The device has further a retractable sleeve 30 which when pushed forward covers stent 28 and prior to expansion of the stent is pulled rearward whereby the stent is exposed.

The rigidity of the device is maintained by means of a wire 32 which is inserted within tube 22 and which terminates at a ring portion 34 for pulling the wire out after the catheter has been placed inside the urethra.

Reference is now being made to FIG. 3 showing the front portion of a catheter 40 having a portion 42 holding a stent 44. The windings of stent 44 when in the first state shown in FIG. 3(a) are overlapping one another. As can be seen, catheter 40 has a plurality of openings 46 at portion 42 within the external tubing, which is the liquid ducting tube. The catheter 40 comprises stopper means 48 and 50 which hold stent 44 within portion 42. Upon injection of a warm liquid into liquid ducting tube of the catheter, warm liquid exits openings 46 and consequently the stent expands, as shown in FIG. 3(b), to form an essentially continuous cylindrical tube having a diameter equal or somewhat above that which is necessary to allow free passage of urine through the urethra. Owing to the fact that the windings in the stent in its first, soft state shown in FIG. 3(a), there is essentially no change in length following expansion of the stent. This ensures that there are essentially no longitudinal displacement of the stents which may avoid injuries to the surrounding tissues which may result from such a movement.

Reference is now being made to FIG. 4 showing a stent in accordance with another embodiment. In this embodiment there is no overlapping in the different windings of stent 48, which is shown in its soft state in FIG. 4(a), and as a result, when the stent expands, as shown in FIG. 4(b), it shortens in length.

A specific use of the stent of the invention is for the purpose of relief of a prostatic obstruction.

FIG. 5 depicts the manner of deployment of a stent of the kind shown in FIG. 1. The catheter 62 with a sleeve 64 coveting the stent at its front end is inserted into the urethra until the front end 66 of the catheter comes to rest within the bladder as shown in FIG. 5(a). In order to avoid pain which can be associated with such a procedure, the catheter may be lubricated by a soothing or a local anesthetic gel, as known per se. Once in this position, as shown in FIG. 5(b), pressure is applied to pressure tube 68, e.g. by means of syringe 70, which causes expansion of balloon 72. The entire catheter is pulled backward until the balloon comes to rest against the bladder's neck. The sleeve 64 is then pulled rearward, as shown also in FIG. 5(b), exposing stent 72 held on the catheter in its first state, close to the front end of the catheter.

Figure 5C:
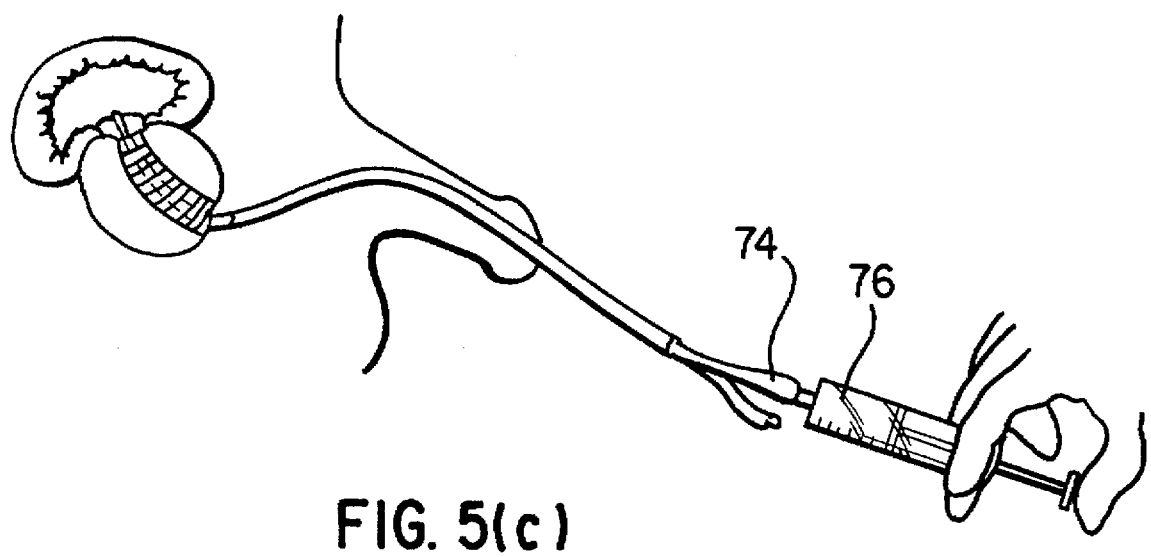
Figure 5D:
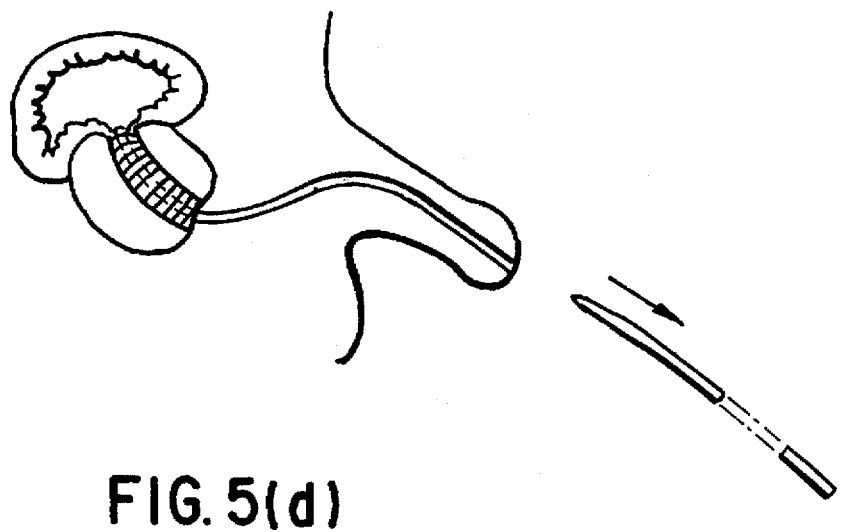

At this state, as shown in FIG. 5(c), warm liquid is applied to liquid ducting tube 74 by a source, e.g. syringe 76. The warm liquid exits through openings at the portion holding the stent and brings to expansion of the stent and to its deployment within the portion of the urethra passing through the prostate. As can be seen in FIG. 5(d), the stent can then be removed leaving the stent within the urethra.

For removal, the catheter may be reinserted to the urethra, then a cold liquid may be injected into the liquid ducting tube, whereby the stent shrinks to its first state in which it can be removed by the use of a grasper, e.g. such included within a cystoscope.

We claim:

1. A device for deployment of a stent in a predetermined part of the urethra, comprising:

a catheter having a front end adapted for insertion into the urethra and a rear end, and comprising at least one pressure tube and at least one liquid ducting tube; said pressure tube being connected to an expandable balloon which is proximal to the front end of the catheter and which is adapted for expansion within the bladder, said pressure tube being connectable at its rear end to a source of pressurized fluid; said liquid ducting tube having openings at a portion thereof rearward to and at a distance from said balloon and being connectable at its rear end to a liquid source; said portion holding a stent being a spiral band, which is made of a shape memory alloy having a first state in which said alloy is soft and substantially deformable and a second state in which said alloy has super-elastic properties and is substantially non-deformable, in which second state the stent assumes a diameter such that it can support the urethra's walls, the shape memory alloy being such that once it assumes said second state it remains in that state at physiological body temperature; said sent being coiled on said portion and is in its soft state and having windings in said first state which are at least partially overlapping whereby the total length of the stent does not change during transition from the first to the second state; the part of the urethra where said stent is being deployed being determined by said distance.

2. A device according to claim 1, wherein the catheter comprises a retractable sleeve adapted to cover the stent when coiled on said portion prior to deployment thereof.

3. A device according to claim 1, wherein the stent is made of a two-way shape memory alloy having a chemical composition represented by the following formula:

$$Ni_l Ti_m A_n$$

wherein

A represents Ni, Co, Fe, Cr or V 1, m, and n representing the proportions of the metal ions within the alloy, the value of 1, m and n totalling 1 and being about as follows:

l=0.5 m=0.5−n n=0.003 to 0.02.

4. A stent according to claim 1, wherein the transition from the first state to the second state occurs within a temperature range of 39° C.–55° C., with the transition between the two states occurring over a temperature range of 1°–4° C.

5. A stent according to claim 1, wherein the second transition temperature is within the range of about 20°–32° C.

6. A device according to claim 1, wherein the stent has a diameter at the first state of about 3–7 mm and a diameter at the second state of about 8–14 mm, said band having a width of about 1–6 mm and a thickness of about 0.1–0.5 mm.

* * * * *